US006408845B1

(12) United States Patent
Pereira et al.

(10) Patent No.: US 6,408,845 B1
(45) Date of Patent: Jun. 25, 2002

(54) RESPIRATORY FILTER

(76) Inventors: Michael Pereira, 33 Booth Ave., Warwick, RI (US) 02893; Anthony Ricci, 149 Cardinal Rd., Cranston, RI (US) 02921; Pierre Legare, RR2, Addison, Ontario (CA), K0E 1A0

( * ) Notice: Subject to any disclaimer, the term of this patent is extended or adjusted under 35 U.S.C. 154(b) by 0 days.

(21) Appl. No.: 09/081,144

(22) Filed: May 19, 1998

Related U.S. Application Data

(60) Provisional application No. 60/047,119, filed on May 19, 1997.

(51) Int. Cl.[7] ........................ A61M 16/00; A62B 27/00; A62B 9/00; C08B 3/00; C08B 5/00

(52) U.S. Cl. ........................... 128/202.22; 128/202.27; 128/205.23; 128/205.29; 128/201.17; 128/206.24; 73/40; 55/DIG. 33; 55/DIG. 35; 137/908; 251/339; 251/349; 251/354

(58) Field of Search ....................... 128/202.27, 205.28, 128/205.29, 206.12, 206.16, 206.17, 206.21, 201.23, 201.14, 202.22, 205.23, 205.25, 206.14, 206.23, 206.24, 206.28; 73/37, 40; 55/DIG. 33, DIG. 35; 137/908; 251/339, 349, 354

(56) References Cited

U.S. PATENT DOCUMENTS

| | | | | | |
|---|---|---|---|---|---|
| 1,596,060 | A | | 8/1926 | Mase | |
| 2,420,372 | A | * | 5/1947 | Heidbrink | 73/40 |
| 2,449,053 | A | * | 9/1948 | Burns et al. | 73/40 |
| 2,738,669 | A | * | 3/1956 | Silverman et al. | 73/40 |
| 2,970,594 | A | | 2/1961 | Doak | |
| 3,250,873 | A | | 5/1966 | Kudlaty et al. | |
| 3,433,455 | A | * | 3/1969 | Cook | 251/339 |
| 3,486,366 | A | * | 12/1969 | Jackson | 73/40 |
| 3,504,542 | A | * | 4/1970 | Blevins | 73/40 |
| 3,580,051 | A | * | 5/1971 | Blevins | 73/40 |
| 4,146,025 | A | * | 3/1979 | Warneke et al. | 128/202.13 |
| 4,494,538 | A | * | 1/1985 | Ansite | 128/205.25 |
| 4,559,939 | A | | 12/1985 | Levine et al. | |
| 4,765,325 | A | * | 8/1988 | Crutchfield | 128/202.13 |
| 4,807,614 | A | | 2/1989 | van der Smissen et al. | |
| 4,832,011 | A | * | 5/1989 | Busch | 128/202.13 |
| 4,846,166 | A | * | 7/1989 | Willeke | 128/200.24 |
| 4,914,957 | A | * | 4/1990 | Dougherty | 73/40 |
| 4,964,900 | A | | 10/1990 | Thompson et al. | |
| 5,299,448 | A | * | 4/1994 | Maryyanek et al. | 73/40 |
| 5,328,152 | A | * | 7/1994 | Castle | 251/229 |
| 5,364,540 | A | | 11/1994 | Sciuto | |
| 5,567,230 | A | * | 10/1996 | Sinclair | 95/273 |
| 5,617,849 | A | * | 4/1997 | Springett et al. | 128/206.24 |
| 5,647,356 | A | * | 7/1997 | Osendorf et al. | 128/206.17 |

FOREIGN PATENT DOCUMENTS

| | | |
|---|---|---|
| DE | 3006823 | 9/1981 |

* cited by examiner

*Primary Examiner*—John G. Weiss
*Assistant Examiner*—Joseph F. Weiss, Jr.
(74) *Attorney, Agent, or Firm*—Sampson & Associates

(57) ABSTRACT

An improved respirator filter assembly includes an integral fit seal check mechanism easily controlled by the user. Upon release, the seal check mechanism permits free airflow through the filter assembly. The seal check mechanism includes an air passageway having a sealing rim and a blocking member which is selectively movable between engaged and disengaged positions relative to the sealing rim. A spring element is disposed to releasably maintain the blocking member in the disengaged position during filter assembly operation, wherein a user may actuate the blocking member against the bias of the spring element to move the blocking member into the engaged position to substantially prevent entry of air into the air passageway during seal checking.

20 Claims, 4 Drawing Sheets

RESPIRATORY FILTER

The instant application claims the benefit of priority under 35 USC 119(e) of U.S. Provisional application Ser. No. 60/047,119, filed May 19, 1997.

TECHNICAL FIELD

The present invention relates to personal safety inhalation equipment, particularly breathing mask filters or respirators. More particularly, the present invention relates to an improved filter assembly with built-in seal check mechanism configured to enable rapid, effective negative pressure safety seal checks.

BACKGROUND OF THE INVENTION

Negative pressure user seal checks are normally performed on personal air respirators by blocking the inlet portion of the filter cartridge and withdrawing air from the mask apparatus. A tight seal stops incoming air from leaking past the mask, creating a clearly detectable vacuum effect. A leaky seal results in a limited vacuum effect and a continuing flow of air into the mask.

To accomplish this test, the main air passage is blocked off, as with a separate structure such as a flat piece of cardboard or plastic applied against the outer surface of the filter, or by covering the inlet of the filter with the palm(s) of the user's hand(s), and the user inhales as deeply as necessary to effect a collapsing of the respirator mask, due to the vacuum, which signals a good fit. The user's thumbs may also be used to block the main air passage; however, the diameter of the apertures to be covered is normally larger than most user thumbs, providing a less-than-perfect seal for this very important personal safety equipment check.

However, problems arise from the difficulty in preventing air flow into the mask. These problems may arise from the imperfect seal effected by the cardboard or plastic, or the inability to use one's hands to accomplish an effective seal. The latter often happens when the hands are dirty or gloves are worn.

An improvement (see FIG. 3) to this method is known in which a cover 100 having a small aperture 102 is snap-fit into place over a cartridge 104. However, the free airflow cross-sectional area of aperture 102 may in some instances be smaller than the free airflow cross-sectional area of cartridge 104, so it may become desirable to remove cover 102 from cartridge 104 for use. This action may disturb the fit of the mask, occasionally necessitating a repeat of the mask fit test procedure.

BRIEF DESCRIPTION OF THE DRAWING FIGURES

The features and advantages of the present filter assembly will be more clearly appreciated from the following description of the preferred embodiments of the invention taken in conjunction with the accompanying drawing figures, in which like reference numerals indicate like elements, and wherein.

SUMMARY OF THE INVENTION

According to one aspect of the present invention, a seal check mechanism for a respirator includes:

- an air passageway in the respiratory filter, the air passageway having a sealing rim;
- a blocking member selectively movable between engaged and disengaged positions relative to the sealing rim; and
- a spring element disposed to releasably maintain the blocking member in the disengaged position during respirator operation;
- wherein the blocking member is user actuatable against the bias of the spring element to move the blocking member into the engaged position to substantially prevent entry of air into the air passageway during seal checking.

In a second aspect of the present invention, a method for fabricating a seal check mechanism for a respirator includes the steps of:

- providing an air passageway in the respirator having a sealing rim;
- providing a blocking member that is selectively movable between engaged and disengaged positions relative to the sealing rim; and
- providing a spring element disposed to releasably maintain the blocking member in the disengaged position during filter assembly operation, wherein the blocking member is user actuatable against the bias of the spring element to move the blocking member into the engaged position to substantially prevent entry of air into the air passageway during seal checking.

In a third aspect of the present invention, a method for seal checking a respirator includes the steps of:

- providing the respirator, with a filter assembly including:
  - an air passageway having a sealing rim;
  - a blocking member proximate the rim wherein the blocking member is selectively movable between engaged and disengaged positions relative to the sealing rim;
  - a spring element in operative engagement with the blocking member to releasably maintain the blocking member in the disengaged position during filter assembly operation;
- actuating the blocking member against the bias of the compression force element to move the blocking member into the engaged position; and withdrawing air from the filter assembly wherein a partial vacuum is created within the respirator in the event of a seal between the respirator and a user.

DETAILED DESCRIPTION OF THE PREFERRED EMBODIMENT

Figure 1:
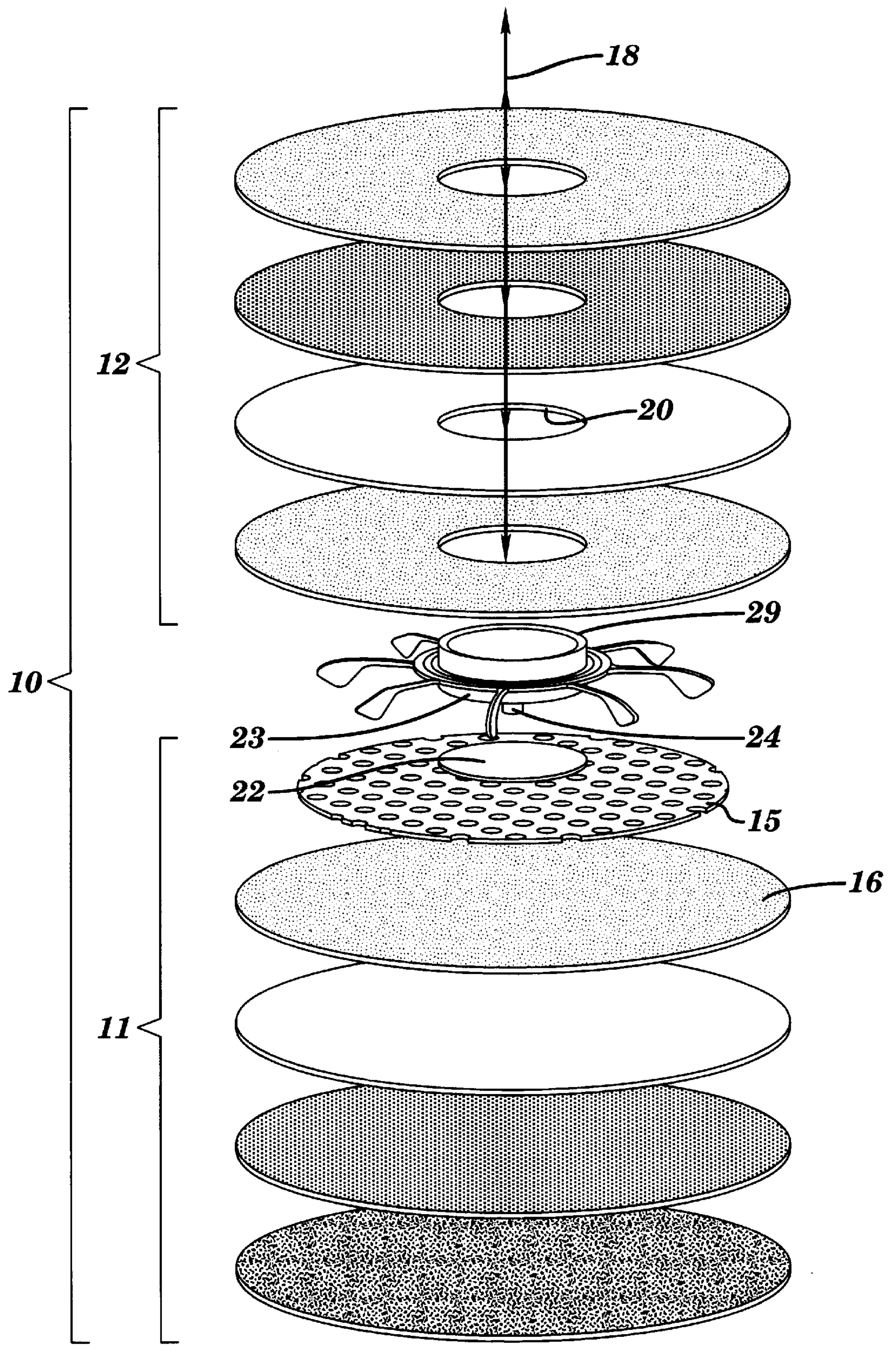
FIG. 1 illustrates an exploded view of the filter assembly of the present invention.
Figure 4:
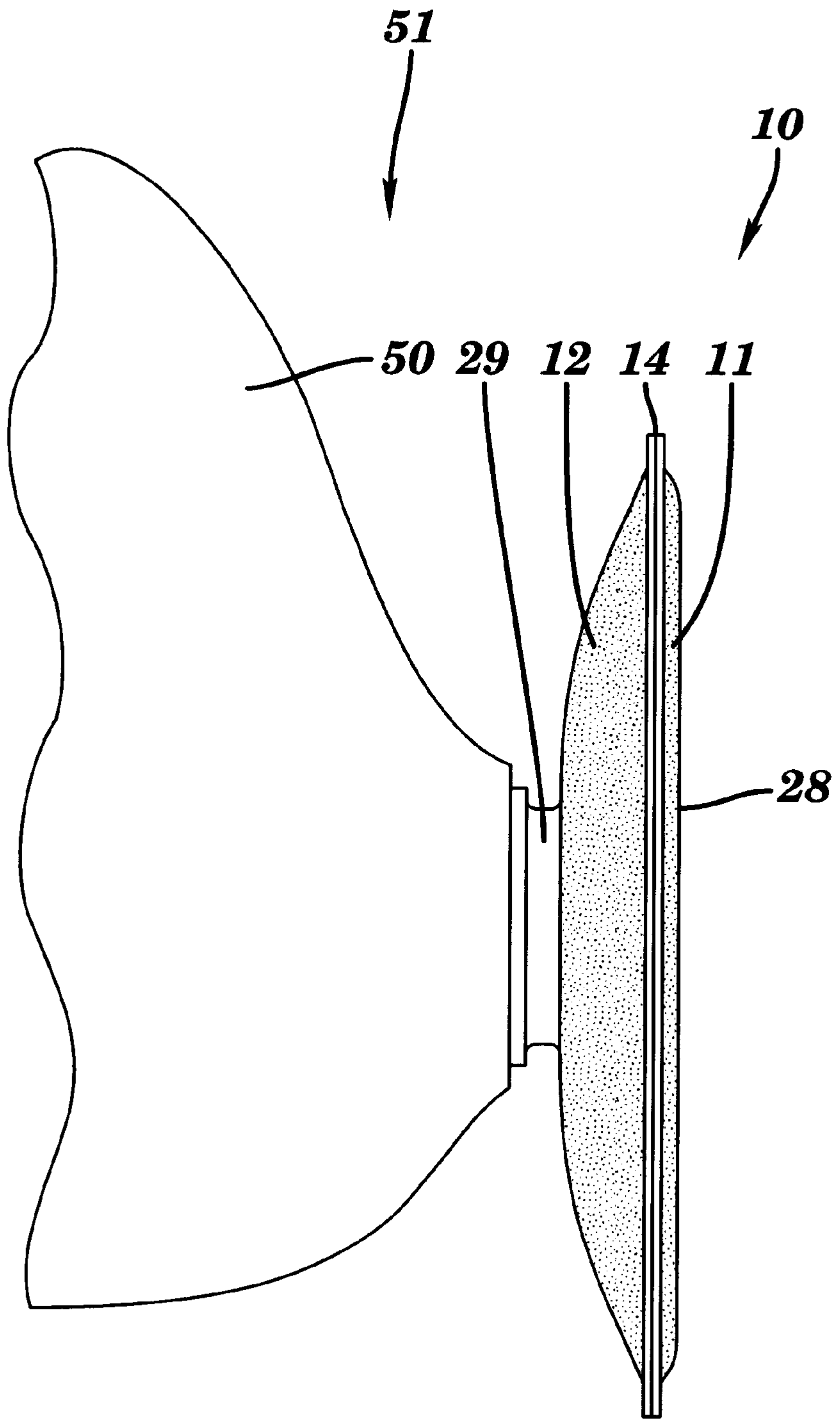
FIG. 4 is an elevational view of the filter assembly of FIG. 1.

Briefly described, the present invention allows negative pressure user seal checking to be performed on a respirator 51 (FIG. 4) with greater ease and more confidence than permitted by the prior art methods and filters. The user simply collapses a spring-loaded air passageway blocking member 22 (FIG. 1) disposed in a mask filter or filter assembly 10 (FIGS. 1 and 4). This blocking member is positioned over the sealing rim portion of a tube or air passageway 17 (FIG. 1) thus sealing off air flow 18 into the respirator 51 at the filter assembly 10.

Figure 2:
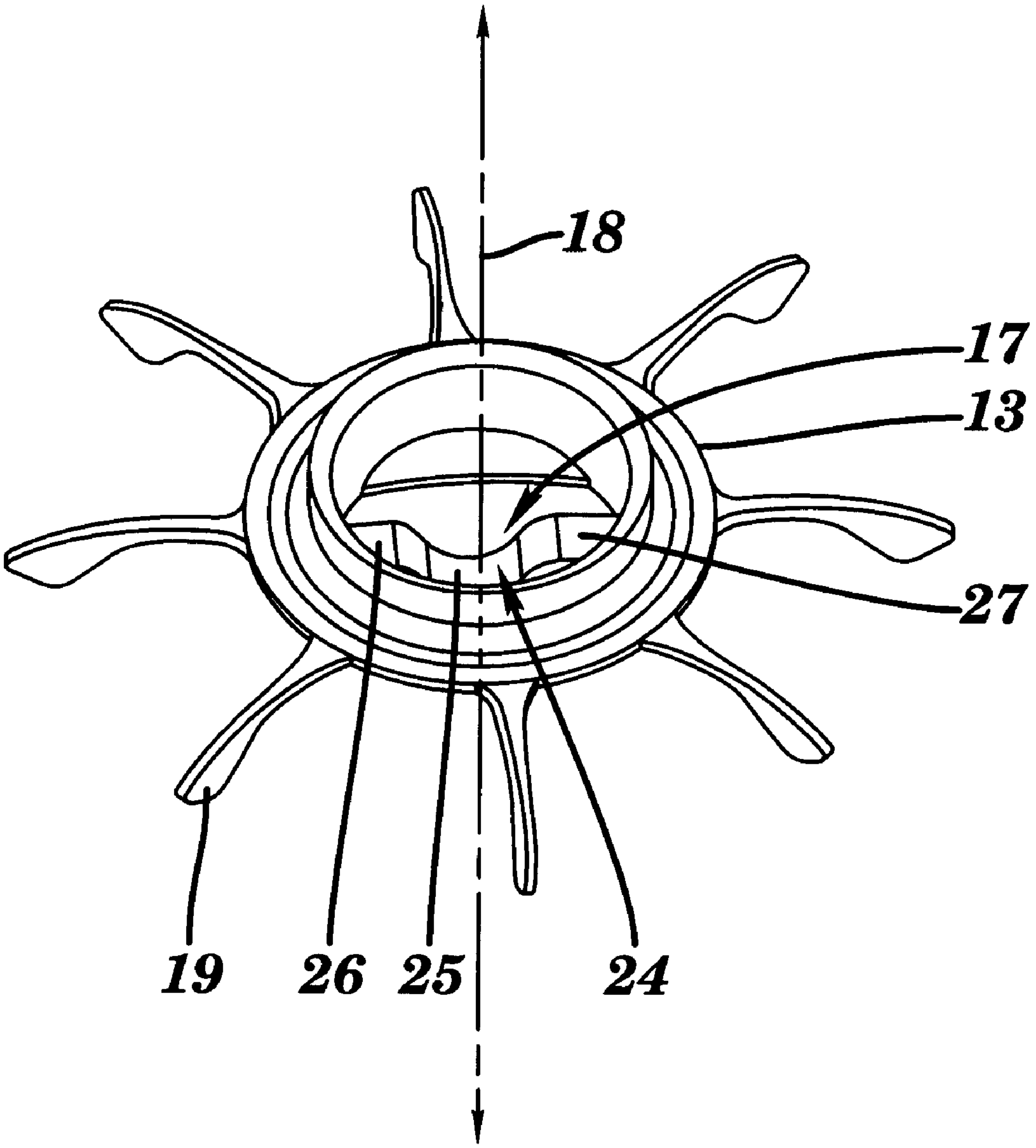
FIG. 2 illustrates in greater detail a portion of the filter assembly shown in FIG. 1.
Figure 3:
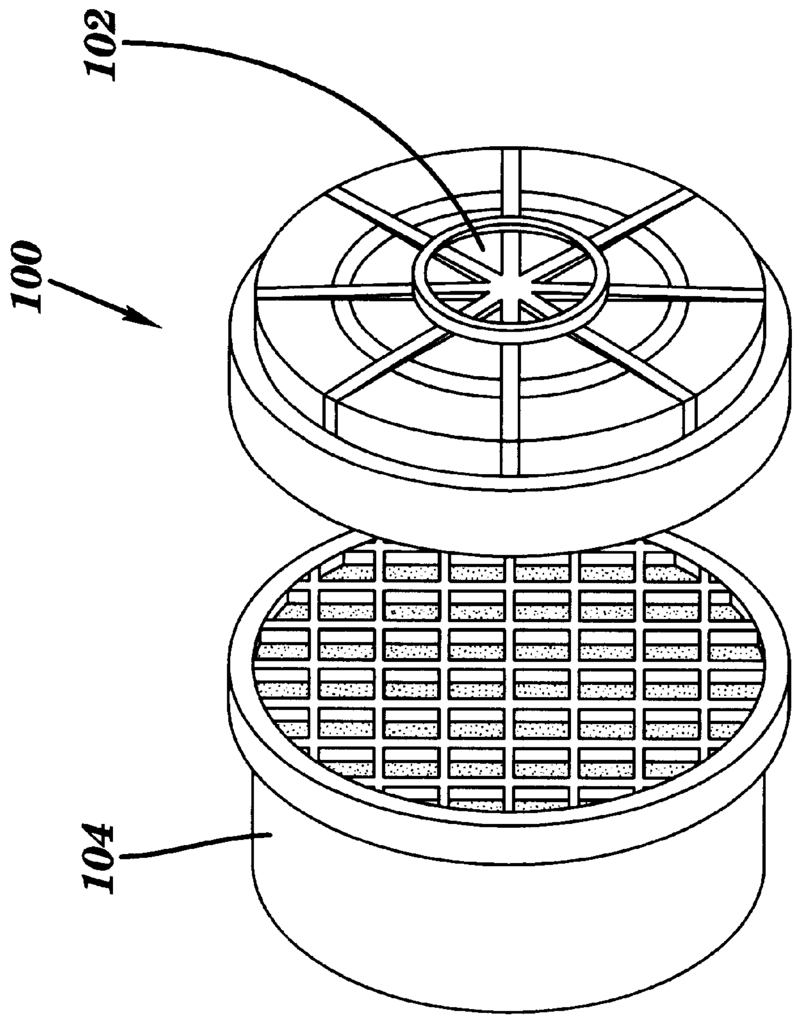
FIG. 3 PRIOR ART
FIG. 3 illustrates a known area reducing cover.

Turning now to the drawings in greater detail, as shown in FIGS. 1, 2, and 4, the filter assembly 10 comprises respective first and second plurality of superposed air permeable filter materials 11, 12 and a central support or "spider member" 13 disposed between the filter materials 11, 12. The filter materials 11, 12 may include various components, such as fabrics, webs, meshes, foams, etc. of various porosity, of the type commonly used in the filtration industry. The filter materials 11 and 12, with the exception of perforate stiffener 15, (discussed hereinbelow) are sealed about the outer periphery 14 thereof as best shown in FIG. 4.

In a preferred embodiment, as shown in FIG. 1, first filter materials 11 also include a planar, perforate member or stiffener member 15 fabricated from a semi-rigid material, such as, for example, cardboard, plastic and the like. The stiffener member 15 is superposed with the other layers of the first filter materials 11, to serve as a support therefore. In a particularly preferred embodiment, stiffener member 15 is disposed between the spider 13 and an inner layer 16 of the first filter materials 11 as shown to provide a firm support for blocking member 22 as will be discussed in greater detail hereinbelow.

The spider 13 may be formed from a wide range of materials; a moldable plastic material is preferred. As best shown in FIG. 2, spider 13 is provided with a an air passageway or tube 17 including a filter connection portion 29 which may include filter connection portions, not shown, for engaging a mask or face piece assembly 50 (FIG. 4). Air may freely flow through tube 17 along a airflow path indicated by double-ended arrow 18 into and out of the mask or face piece assembly 50 (FIG. 4). The mounting portions may be configured as either threaded or bayonet mounts, or otherwise as may be determined by the mask filter mounts (not shown), not forming a novel part of the present invention. The arms 19 of the spider 13 serve to separate the unsealed portions of first and second filter materials 11, 12.

The second filter materials 12 include central apertures 20 which are sealed to the outer surface of the air passageway 17 of spider 13, permitting the filter connection portion 29 of air passageway 17 to extend therethrough for mounting to the face piece assembly 50. As shown, the first filter materials 11 preferably do not include such a central aperture.

The blocking member or air impermeable check fit test disk 22 is centrally disposed on perforate member 15 in superposed alignment with a sealing rim 23 of the air passageway 17 of spider 13. The blocking member is preferably formed of a planar plastic material, although any planar air blocking material may be used. Air passage need not be completely blocked by the blocking member 22 and sealing rim 23 to effectively seal the filter assembly 10 for the purposes of the fit check test procedure.

Lying across the air passageway 17 and extending outward of sealing rim 23 to contact disk 22 is a spring element 24. A person having ordinary skill in the art will recognize that a wide range of configurations and materials may be used for spring 24.

In one preferred embodiment, a leaf spring center element 25 having a generally "C" shaped medial portion disposed between two or more elongated arm portions 26, 27, is provided. In this preferred embodiment, leaf spring element 25, including elongated arm portions 26 and 27 are formed integrally with the spider 13 and lie at least partly within air passageway 17, extending across sealing rim 23. Other spring materials may include, for example, metals.

The blocking member 22 may be attached to stiffener member 15 or to spring element 24, as may be desired, by any common mechanism in order to retain the blocking member 22 in the desired superposed position relative to air passageway 17. Examples of such joining mechanisms include electronic weld joining, gluing, and staking, or the like.

After assembling the filter assembly to a mask or face piece assembly 50 (FIG. 4), the user can perform a negative pressure seal check simply by depressing the portion 28 of the filter media superposed with the blocking member 22 with either the finger tips, thumbs, or palms.

This portion 28 of the filter media superposed with the blocking member 22 may include less than 50 percent, and preferably about 5 to 10 percent, of the total exposed surface area of the filter materials 11 and 12. Depressing the filter media in this area causes the stiffener member 15 and the blocking member 16, which are assembled to each other in the preferred embodiment, to move forward, collapsing the spring element 24 of the spider 13 against rim 23. The blocking member 22 causes the spring element 24 to readily collapse with only slight, general frontal pressure in order to permit the blocking member to seal against the sealing rim 23 of the spider 13, thus effectively blocking airflow 18 into the face piece assembly 50 from the filter assembly 10.

When any necessary face piece assembly adjustments are completed and the test is finished to the satisfaction of the user, release of the slight frontal pressure permits the spring element 24 to push the blocking member 22 back to its original position away from the spider 13 sealing rim 23 and restraining it in its normal position where it does not block airflow 18.

Although only preferred embodiments of the present invention are specifically illustrated and described herein, it will be appreciated that many modifications and variations of this present invention are possible in light of the above teachings and within the purview of the appended claims without departing from the spirit and intended scope of the invention.

We claim:

1. A seal check mechanism for a respirator, comprising:

an air passageway in the respirator, the air passageway having a sealing rim;

a blocking member selectively movable between engaged and disengaged positions relative to said sealing rim; and a spring element disposed to releasably maintain said blocking member in said disengaged position during respirator operation;

wherein said blocking member is user actuatable against the spring element's bias to move said blocking member into said engaged position to substantially prevent entry of air into said air passageway during seal checking.

2. The seal check mechanism of claim 1, wherein said spring element extends between said blocking member and said sealing rim.

3. The seal check mechanism of claim 2, wherein said mechanism is adapted for use with air permeable filter material extending from a periphery of said blocking member and being sealed in an air impermeable manner to said air passageway, wherein any air passing through said air passageway passes through said filter material.

4. The seal check mechanism of claim 3, wherein user actuation is accomplished by compressing at least a portion of the filter material towards said sealing rim.

5. The seal check mechanism of claim 3, wherein said mechanism is adapted for use with a support member extending radially from a periphery of said air passageway to support at least a portion of the filter material in superposed spaced relation to said sealing rim.

6. The seal check mechanism of claim 1, wherein said spring element comprises a leaf spring extending across said sealing rim, said leaf spring having a medial portion adapted to engage said blocking member.

7. The seal check mechanism of claim 6, wherein said medial portion is substantially "C" shaped.

8. A filter assembly for a respirator, said filter assembly comprising:

a seal check mechanism for a respirator, including:

an air passageway in the respirator having a sealing rim;

a blocking member selectively movable between engaged and disengaged positions relative to said sealing rim; and a spring element disposed to releasably maintain said blocking member in said disengaged position during filter assembly operation;

wherein said blocking member is user actuatable against the bias of said spring element to move said blocking member into said engaged position to substantially prevent entry of air into said air passageway during seal checking; and filter material sealably fastened to said air passageway and extending to a periphery of said blocking member, wherein air passing through said air passageway passes through said filter material.

9. The filter assembly of claim 8, wherein said filter material is compressible against the bias of said spring element to move said blocking member into said engaged orientation.

10. The filter assembly of claim 8, wherein at least a portion of said filter material is maintained in superposed relation to said sealing rim, said blocking member being disposed on said at least a portion of said filter material.

11. The filter assembly of claim 10, wherein said at least a portion of said filter material comprises less than 50 percent of the filter assembly's total exposed filter material surface area.

12. The filter assembly of claim 11, wherein said at least a portion of said filter material comprises approximately 5 to 10 percent of the total exposed filter material surface area.

13. The filter assembly of claim 10, wherein said filter material further comprises a stiffener member, said blocking member being disposed thereon.

14. The filter assembly of claim 8, wherein said spring element extends between said sealing rim and said blocking member.

15. The filter assembly of claim 8, wherein said spring element comprises a leaf spring extending across said sealing rim.

16. The filter assembly of claim 8, further comprising a support member extending radially from a periphery of said air passageway to support at least a portion of said filter material in superposed spaced relation to said sealing rim.

17. The filter assembly of claim 16, wherein said filter material further comprises a plurality of filter layers in superposed relation to one another.

18. The filter assembly of claim 17, wherein said support member is disposed between portions of two of said plurality of filter layers to maintain said portions in superposed, spaced relation to one another.

19. A method for fabricating a seal check mechanism for a respirator, said method comprising the steps of:

providing an air passageway in the respirator having a sealing rim;

providing a blocking member that is selectively movable between engaged and disengaged positions relative to said sealing rim; and providing a spring element disposed to releasably maintain said blocking member in said disengaged position during filter assembly operation, wherein said blocking member is user actuatable against the bias of said spring element to move said blocking member into said engaged position to substantially prevent entry of air into said air passageway during seal checking.

20. A method for seal checking a respirator, said method comprising the steps of:

providing the respirator with a filter assembly including:

an air passageway having a sealing rim;

a blocking member proximate said rim wherein the blocking member is selectively movable between engaged and disengaged positions relative to said sealing rim;

a spring element in operative engagement with the blocking member to releasably maintain said blocking member in said disengaged position during filter assembly operation;

actuating said blocking member against the bias of said spring element to move said blocking member into said engaged position; and withdrawing air from said filter assembly wherein a partial vacuum is created within the respirator in the event of a seal between the respirator and a user.

* * * * *